United States Patent [19]
Moore

[11] Patent Number: 5,830,682
[45] Date of Patent: *Nov. 3, 1998

[54] PREPARATION OF IMMORTALIZED CELLS

[75] Inventor: Emma E. Moore, Seattle, Wash.

[73] Assignee: ZymoGenetics, Seattle, Wash.

[*] Notice: The term of this patent shall not extend beyond the expiration date of Pat. No. 5,683,906.

[21] Appl. No.: 770,895

[22] Filed: Dec. 13, 1996

Related U.S. Application Data

[63] Continuation-in-part of PCT/US95/11484 Sep. 11, 1995, continuation-in-part of Ser. No. 479,882, Jun. 7, 1995, Pat. No. 5,648,219, and a continuation-in-part of Ser. No. 303,983, Sep. 9, 1994, Pat. No. 5,683,906.

[51] Int. Cl.$^6$ .............................. C12N 5/06; C12Q 1/02
[52] U.S. Cl. ........................... 435/29; 435/352; 435/354; 435/377; 435/384
[58] Field of Search .................................... 435/352, 354, 435/377, 384, 7.21, 29

[56] References Cited

U.S. PATENT DOCUMENTS 5,683,906  11/1997  Moore ...................................... 435/325

OTHER PUBLICATIONS

Thompson, DL et al. J. Bone and Mineral Res. 11(supp. 1): S108. abstract #54, Aug. 1996.

*Primary Examiner*—David Saunders
*Assistant Examiner*—F. Pierre VanderVegt
*Attorney, Agent, or Firm*—Townsend and Townsend & Crew

[57] ABSTRACT

All lines have been prepared from growth suppressor gene deficient animals. The cells include immortalized precursor cells and differentiated cells such as osteoclast precursors, osteoblast precursors, megakaryocytes, osteoclasts, osteoblasts, pancreatic α-cells, pancreatic β-cells, pancreatic δ-cells, adipocytes, macrophages, chondrocytes, dendritic cells, hepatocytes, myocytes and prostatic cells. The cells are useful for constructing cDNA and protein libraries, screening agonists and antagonists of compounds and factors that affect metabolic pathways of specific cells and generating cell-specific antibodies.

13 Claims, 1 Drawing Sheet

PREPARATION OF IMMORTALIZED CELLS

This application is a continuation-in-part of Ser. No. PCT/US95/11484, filed 11 Sep. 1995, and a continuation-in-part of Ser. No. 08/479,882 filed Jun. 7, 1995, and a continuation-in-part of Ser. No. 08/303,983 filed Sep. 9, 1994. All of the above applications are incorporated by reference in their entirety for all purposes.

TECHNICAL FIELD

The present invention resides in the field of cell biology.

BACKGROUND OF THE INVENTION

Cell lines have played an important role in the development of molecular and cellular biology, particularly in the elucidation of intracellular activities, the effects of extracellular molecules and cell-cell interactions. Cell lines are established stepwise by: explantation of tissue containing a heterogeneous cell population; separation of the cells; isolation of a cell clone; and culturing the cell clone so that the total cell number increases over several generations and the population is uniform in its lineage. Cell cultures may be started from primary tissue culture explants, where heterogeneous cell types separate or migrate from the tissue in liquid medium; or by enzyme digestion of a tissue, resulting in dispersed cell suspensions.

Differentiation is the process of maturation of cells. It is a progressive and dynamic process, beginning with pluripotent stem cells and ending with terminally differentiated cells that progress no further down the cell lineage pathway. A cell's function, phenotype and growth characteristics are affected by the cell's degree of differentiation.

Cells that can be continuously cultured are known as immortalized cells. Immortalized cells have advantages over non-immortalized cells because they can be cultured to provide large numbers of uniform cell populations. Immortalized cells are routinely used for understanding intracellular activities such as the replication and transcription of DNA, metabolic processes and drug metabolism. Investigation of cellular transmembrane activities such as ligand-receptor interactions and signal transduction are facilitated by access to specific cell types. Immortalized cells are also useful in the development of an understanding of specific cell-cell interactions such as adhesion, invasion and contact inhibition. However, many cell types have remained difficult to isolate and continuously culture, such as cells of the osteoclast lineage, hematopoietic-CD34$^+$ stem cells, mesenchymal stem cells, dendritic cells and other cell precursors that are at early stages of differentiation. In addition, many differentiated cells lose some of their differentiated properties in order to regain or retain the ability to proliferate. Thus many of the available cell lines that can be continuously cultured do not express the differentiation functions that make them valuable tools.

One such cell type that has been difficult to immortalize is the dendritic cell, an antigen presenting cell, and its precursors that are at early stages of differentiation. Steinman et al., WO 93/20185, have disclosed methods for isolating primary dendritic cells and their precursors from tissue. Granucci et al., WO 94/28113, and Paglia et al., J. Exp. Med. 178:1893–1901, 1993, have disclosed cell lines isolated from primary cultures and infected with retroviral vectors to immortalize the cells.

Dendritic cells are the most potent antigen presenting cells (APCs) in the immune system. Dendritic cells are the only cells that present antigen to, and activate, naive CD4$^+$ T cells in vivo (Levin et al., J. Immunol. 151:6742–6750, 1993). Dendritic cells are found in primary and secondary lymphoid organs (e.g., thymus, lymph nodes, tonsils, Peyer's patches, and spleen), as well as in non-lymphoid organs and tissues (e.g., heart, liver, lung, gut, and in the skin as epidermal Langerhans cells). Dendritic cells are also prevalent in afferent lymph, but are rare in blood. For reviews, see Steinman, Ann. Rev. Immunol. 9:271–296, 1991 and Knight et al., J. Invest. Dermatol. 99:33S–38S, 1992.

Dendritic cells are thought to originate from a single hematopoietic progenitor cell. As progenitor cells begin the process of differentiation they migrate to selected tissue and/or organs, where they appear to undergo additional differentiation. If isolated from tissue, dendritic cells are immature; that is, the cells are not fully differentiated, are inefficient at antigen presentation, express low levels of MHC Class II molecules and do not stimulate proliferation of T-cells in an allogenic mixed leukocyte reaction (MLR). However, when immature dendritic cells are exposed to foreign proteins, they become capable of taking up and presenting soluble antigen via newly synthesized MHC Class II molecules, and simultaneously leave their tissue residence and migrate to lymph nodes and spleen. After migrating from the origin tissue, the dendritic cells are mature; that is, they exhibit high levels of MHC Class II, accessory and co-stimulatory molecules, as well as full APC function (Steinman, ibid., 1990 and Ibrahim et al., Immunol. Today 16:181–186, 1995). Antigen uptake and processing by dendritic cells are not well understood, however, because of the inability to isolate and culture sufficient numbers of homogeneous dendritic cells or dendritic precursor cells.

Dendritic cells have been implicated as the primary causative cells in a number of different diseases that involve immune responses, including contact sensitivity, tumor immunity, HIV-1 infection and autoimmunity (e.g., Type I diabetes, multiple sclerosis and rheumatoid arthritis). These cells are believed to play a role in graft rejection, where cells from the allograft migrate into the lymphoid organs of the recipient and initiate a deleterious immune response.

Therefore, there remains a need in the art for new methods to immortalize cells and establish cell lines that can be continuously cultured. There also remains a need for certain types of immortalized stem cells, precursor cells and fully differentiated cells that retain their differentiated properties while continuously being cultured.

SUMMARY OF THE INVENTION

It is an object of the present invention to provide methods for preparing immortalized cells from a tissue of a growth suppressor gene deficient animal.

It is a further object of the invention to provide methods for preparing immortalized cells that express a set of differentiation markers not expressed by fibroblast cells.

It is a further object of the invention to provide immortalized cells, including immortalized cells that express a set of differentiation markers not expressed by fibroblast cells.

Another object of the present invention is to provide differentiated cells of a predetermined type, and immortalized cells that can be stimulated to differentiate into cells of the predetermined type.

The methods of the present invention comprise the steps of culturing a tissue from a growth suppressor gene deficient animal in a medium; isolating component cells from the cultured tissue; assaying at least a portion of the isolated cells for expression of a set of differentiation markers characteristic of a cell-type of interest, to identify a subset of said isolated cells, wherein the set of markers is not expressed by fibroblast cells; and selectively culturing cells of said subset of cells to identify an immortalized cell population. Within one embodiment, the portion of the isolated cells is stimulated to differentiate prior to the step of assaying. Within another embodiment, cells of the immortalized population are stimulated to differentiate to provide differentiated cells.

Within one preferred embodiment the growth suppressor gene is p53. Within another preferred embodiment, the tissue is either bone marrow or calvarial bone. Within another preferred embodiment, the cells of the subset of isolated cells are either osteoclast precursors or osteoblast precursors. Within another embodiment the set of differentiation markers is selected from the group consisting of TRAP and calcitonin receptor; ALP, osteocalcin and PTH receptor; cardiac myosin isozyme and cardiac specific creatine kinase isozyme; myosin isozyme and muscle specific creatine kinase isozyme; aggrecan and collagen Type IIB; mpl receptor and acetyl choline esterase; insulin; glucagon and glucagon-like polypeptide; somatostatin; triglyceride and perilipin; non-specific esterase (NSE) and Mac-1; and albumin, liver-specific glucokinase, liver-specific pyruvate kinase and liver isozyme of glycogen synthase.

Within a related aspect of the invention, immortalized cells prepared by the methods disclosed above are provided. In one embodiment the cells are selected from the groups consisting of osteoclast precursors, osteoblast precursors, cardiac muscle precursor cells, skeletal muscle precursor cells, chondrocyte precursors, megakaryocytes, pancreatic α-cell precursors, pancreatic β-cell precursors, adipocyte precursors, macrophages, dendritic cells and hepatocyte precursors. Within another embodiment, cells are selected from the group consisting of osteoclasts, osteoblasts, pancreatic α-cells, pancreatic β-cells, pancreatic δ-cells, adipocytes, chondrocytes, macrophages, dendritic cells and hepatocytes.

It is another object of the present invention to provide an immortalized dendritic cell. The dendritic cells have been deposited at the American Type Culture Collection as JAWS II.

It is a further object of the present invention to provide a dendritic cell that is induced to become an activated dendritic cell. In one embodiment, the dendritic cell is activated using a factor selected from the group consisting of a) tumor necrosis factor- (TNF-α); (b) interferon-γ (IFN-γ); (c) granulocyte macrophage colony-stimulating factor (GM-CSF); (d) interleukin-4 (IL-4); and (e) a combination of (a), (b), (c) or (d).

Another object of the present invention provides for methods for assaying antigen-specific responder cell stimulation comprising activating the dendritic cells, exposing the activated cells to an exogenous antigen, thereby producing antigen-presenting stimulator cells and measuring activation of the responder cells. In one embodiment, the responder cells are naive or primed T cells. In another embodiment, the activation of the responder cells is determined by measuring responder cell proliferation. In another embodiment, the proliferation of the antigen-presenting stimulator cells is inhibited prior to the step of combining with the responder cells. In another embodiment, the proliferation of the antigen-presenting stimulator cells is inhibited by exposure to ( ) irradiation or mitomycin C.

In another aspect, the present invention provides for methods for obtaining a dendritic cells that expresses a heterologous MHC class II protein at the cell surface comprising transfecting the dendritic cells with a polynucleotide encoding a heterologous MHC class II protein and selecting a subset of the dendritic cells that expresses the heterologous MHC class II protein at the cell surface, thereby forming selected MHC class II-specific dendritic cells. In another embodiment, the methods comprise the step of eliminating from the dendritic cell genome any region the encodes endogenous MHC class II molecules. In another embodiment, the methods provide activated the selected MHC class II-specific dendritic cells. In another embodiment, the methods comprise before, during or after the step of activating, blocking endogenous MHC class II protein expressed by the selected MHC class II-specific dendritic cells. In another embodiment, after activation, the methods comprise exposing the selected MHC class II-specific dendritic cells to an exogenous antigen, thereby producing selected MHC class II-specific antigen-presenting stimulator cells with responder cells and measuring the stimulation of the responder cells. In another embodiment, the responder cells are T lymphocytes. In another embodiment, the exogenous antigen is a self or non-self antigen that is involved in a T lymphocyte-mediated response. In another embodiment, the exogenous antigen is an autoantigen. In another embodiment, the exogenous antigen is GAD and the heterologous MHC class II protein is an MHC molecule associated with diabetes.

In a further aspect, the invention provides immortalized growth suppressor gene-deficient mammalian osteoblastic lineage cells characterized by a set of differentiation markers including PTH-induced cAMP expression, osteocalcin expression, alkaline phosphatase expression and bone mineralization activity, wherein on induction with an agent selected from the group consisting of indomethacin, dexamethasone, ascorbic acid and combinations thereof, the osteoblast lineage cells convert to adipocytes characterized by oil red O staining. Preferably, the cell line is p53-deficient mouse cell line. An exemplary cell line is designated 7F2.

The invention further provides methods of using such cell lines in screening compounds for efficacy in treating osteoporosis. A compound being tested is treated with such a cell line and an inducing agent, and conversion of the cell line to adipocytes is monitored. The rate or extent of conversion is inversely related to efficacy of the compound in treating osteoporosis. The invention also provides methods for screening compounds, such as may be found in food or drugs, for undesired side-effects in promoting osteoporosis. In these methods, the compound being tested with the cell line and conversion of the cell line to adipocytes is monitored. The rate or extent of conversion is related to activity in promoting osteoporosis.

In another aspect, the invention provides immortalized prostatic lineage cell lines from a growth suppressor deficient mammal. Preferably the cell lines are from a P53 deficient mouse. The cell lines include epithelial lineage cell lines characterized by expression of cytokeratins. The cell lines also include stromal lineage cell lines characterized by expression of smooth-muscle actin or prolyl-4-hydroxylase.

In another aspect, the invention provides immortalized myocyte lineage cell lines from a growth suppressor deficient mammal. Preferably the cell lines are from a p53 deficient mouse. Such a cell line is characterized by a set of differentiation markers including muscle α-actin mRNA, nuclear proliferating cell nuclear antigen (PCNA) and smooth muscle cell actin. The invention further provides mouse myocyte cells produced by induction of the cell line characterized by a set of differentiation markers including cardiac α-actin mRNA, atrial natriuretic factor, type B natriuretic factor, myosin light chain, α-cardiac myosin heavy chain, phopholamban and spontaneous contractility.

These and other aspects of the invention will become evident upon reference to the following description.

DETAILED DESCRIPTION OF THE INVENTION

Prior to describing the present invention in detail, it may be helpful to define certain terms used herein:

Immature dendritic cell: A dendritic cell that expresses low levels of MHC class II, but is capable of endocytosing antigenic proteins and processing them for presentation in a complex with MHC class II molecules.

Activated dendritic cell: A more mature dendritic cell that expresses high levels of MHC class II, ICAM-1 and B7-2, and is capable of stimulating the proliferation of naive allogeneic T cells in a mixed leukocyte reaction (MLR).

As noted above, the present invention provides methods for preparing immortalized cells. The methods comprise the steps of culturing a tissue from a growth suppressor gene deficient animal in a medium; isolating component cells from the cultured tissue; assaying at least a portion of the isolated cells for expression of a set of differentiation markers characteristic of a cell type of interest to identify a subset of said isolated cells, wherein the set of differentiation markers is not expressed by fibroblast cells; and selectively culturing cells of said subset of cells, wherein said subset of cells is immortalized.

The present invention provides methods of obtaining immortalized cell lines and differentiated cells from a variety of animals, including mammals, birds, fish, insects, reptiles and amphibians. Of particular interest are mammals, including primates; laboratory animals such as rats, mice, rabbits and dogs; and livestock animals such as horses, cows, swine and fowl, and rodents, such as mice, rats and rabbits.

Cells that can be continuously cultured and do not die after a limited number of cell generations are known as "immortalized." A cell that survives for only 20 to 80 population doublings is considered finite (Freshney, *Culture of Animal Cells*, Wiley-Liss, New York, 1994, herein incorporated by reference), and a cell that survives more than 80, preferably at least 100, cell generations is considered immortalized.

Immortalization may be associated with transformation, implying increased tumorigenicity and significant changes in phenotype, but cells may be immortalized without being tumorigenic. The altered ability to be continuously cultured may be due to, for example, a deletion or mutation in one or more of the genes whose products play a role in cell senescence, or overexpression or mutation of one or more oncogenes that override the action of the senescence genes. Expression of genes that result in positive signals for cell proliferation include SV40 large T antigen (Linder et al., *Exp. Cell Res.* 191:1–7, 1990), polyoma large T antigen (Ogris et al., *Oncogene* 8:1277–1283, 1993), adenovirus E1A (Braithwaite et al., *J. Virol.* 45:192–199, 1983), myc oncogene (Khoobyarian et al., *Virus Res.* 30:113–128, 1993), and the E7 gene of papilloma virus Type 16 (McDougall, *Curr. Top. Microbiol. Immunol.* 186:101–119, 1994).

One group of senescence genes is the tumor or growth suppressor genes. These genes are negative regulators of cell proliferation. Inactivation of growth suppressor genes is generally associated with transformation of cells and often results in tumor formation in vivo. Included in this senescence gene group are p53, RB, NF1, p16 and DCC genes (Marshall, *Cell* 64:313–326, 1991).

Animals that are "growth suppressor gene deficient" include those animals that are homozygous for a mutation in a growth suppressor gene, resulting in lack of expression of a functional growth suppressor gene product. Such mutations may arise spontaneously or be introduced. Growth suppressor gene deficient animals, such as mice and other species, may be produced, for example, by a process called homologous recombination, in which a mutated DNA sequence seeks its complement on a chromosome and then recombines to replace a portion of the native allele (Baribault et al., *Mol. Biol. Med.* 6:481–492, 1989 and Bernstein et al., *Mol. Biol. Med.* 6:523–530, 1989).

Briefly, a DNA sequence encoding a growth suppressor gene is modified to prevent expression of a functional gene product. For example, internal stop codons, deletions, frameshifts or some other modification that would terminate translation can be introduced into the DNA sequence of the growth suppressor gene along with a selectable marker. The modified sequence is transfected into embryonic stem cells, and transfected clones identified by selective pressure are screened to identify those cells that have incorporated the modified gene by homologous recombination. The cells containing the modified DNA sequence are implanted into blastocytes, which are subsequently injected into the uteri of pseudopregnant female mice, and the resulting chimeric animals are subjected to a series of back crosses to identify animals that are homozygous for the modified gene (Robertson, *Biol. of Reproduc.* 44:238–245, 1991). In the alternative, growth suppressor gene deficient animals can be obtained commercially, for example, from DNX (Princeton, N.J.), GenPharm International (Mountain View, Calif.) and The Jackson Laboratory (Bar Harbor, Me.). When an animal contains a growth suppressor gene deficiency that prevents the expression of a growth suppressor gene product, it is referred to as a "knockout" animal.

Growth suppressor genes include RB (Horowitz et al., *Proc. Natl. Acad. Sci. USA* 87:2775–2779, 1990 and Hansen et al., *Trends Genet.* 4:125–128 1988), NF1 (Cawthon et al., *Cell* 62:193–201, 1990), p16 (Marx, *Science* 264:1846, 1994) and p53 genes (Nigro et al., *Nature* 342:705–708, 1989). Other growth suppressor genes may, however, be altered to produce animals with growth suppressor gene mutations (Hiti, *Molec. Cell. Biol.* 9:4722–4730, 1989; Gallie, *J. Cell. Biochem.* 32:215–222, 1986; Alt et al., *Cold Spr. Harb. Symp. Quant. Biol.* 51:931–942, 1986; Malcolm, *Molec. Med.* 1:79–84 1984; all herein incorporated by reference). A particularly preferred growth suppressor gene is p53. The physiological role for p53 appears to be in regulation of the cell cycle. While the precise function of the p53 protein has not been elucidated, it is thought to interact with the large T antigen and possibly be a transactivator of transcription (Donehower et al., *Nature* 356:215–221, 1992). Mutations in p53 have been correlated with increased tumorigenicity, and particularly with lung carcinomas, osteosarcomas and lymphoid tumors (Lavigueur et al., *Mol. Cell. Biol.* 9:3982–3991, 1989).

In the methods of the present invention a tissue is excised from a growth suppressor gene deficient animal and placed in a culture medium. Tissue is a composite of heterogeneous cell populations. Examples of tissues include bone marrow, bone, skeletal and cardiac muscle, prostate, pancreas, brain and liver. Tissues usually consist of a mixture of tissue specific cell-types as well as cells found in many tissues, such as fibroblasts.

Component cells are isolated from tissue samples by plating cells at a density sufficiently low that colonies grow from a single cell. When necessary, the tissue is disrupted according to conventional enzymatic or mechanical methods to separate component cells. Cell populations originated from a single cell are referred to as clonal colonies or clonal cell populations.

Methods of isolating cells from tissue are known in the art. See, for example, *Methods In Molecular Biol.: Animal Cell Culture,* 5, Pollard et al. eds., Humana Press, N.J., 1990, which is incorporated herein by reference. For example, osteoclasts, macrophages, and dendritic cells and their precursors may be isolated from bone marrow (for a review, see, for example, Dexter et al., in *Long-Term Bone Marrow Culture:*57–96, Alan R. Liss, 1984). Bone marrow is extracted from a sacrificed animal by dissecting out the femur, removing soft tissue from the bone and cutting off the epiphyses (cortical ends). The bone marrow is removed with a needle and syringe or flushed out with an isotonic solution. The marrow cells are plated at a low density into petri dishes and allowed to attach to the surface of the dish. Clonal colonies are picked and replica plated for continuous culturing and characterization.

Bone marrow contains several different cell types of the myeloid lineage. Therefore, cells may be identified morphologically. For example, immature dendritic cells in one or more phases of their development are loosely adherent to plastic, flattening out with a stellate shape. Cells have a single, rounded nucleus and lack the large granular organelles apparent in macrophages. Frequently, projections are observed protruding from both the adherent and nonadherent cells. Higher magnification reveals a "veiled" morphology.

Cells of the osteoblast lineage may be isolated from bone. Methods for isolating osteoblasts from bone are known in the art (see, for example, Aubin et al., *J. of Cell Biol.* 92:452–461, 1982). One method of isolation uses calvarial bone. The calvaria is excised, rinsed in a medium and minced with scissors. The minced bone is digested with collagenase for a short period of time in medium. The cells are removed by centrifugation and decanting the supernatant, leaving the bone pieces behind. Fetal calf serum is added to inhibit the collagenase digestion. Cells are plated at a low density in an appropriate growth medium, and clonal cell colonies are cultured in replicate for continuous culture and characterization. The collagenase-treated calvaria can also be placed in culture dishes, and osteoblast cells will migrate or "crawl" out from the bone (Robey et al. *Calcified Tiss. Internat.* 37:453–460, 1985). Osteoblasts may also be removed from cancellous bone. For example, femurs are excised from an animal, marrow is expressed, and the bone is placed in an isotonic solution. The femurs are rinsed several times to remove any remaining marrow and soft tissue. The bones are crushed and digested with collagenase as described previously.

Pancreatic $\alpha$, and $\beta$ cells may be isolated by excision of the pancreas and dissociation of individual cells with collagenase or trypsin digestion (Lacy et al. *Diabetes* 16:35, 1967 and Gotoh et al. *Transplantation* 40:437–438, 1985). Methods for the extraction of adipocytes using collagenase (Rodbell, *J. Biol. Chem.* 238:375–380, 1974), isolation of skeletal muscle (Yaffe et al. *Develop. Biol.* 11:300–317, 1965), cardiac muscle (Wolleben et al. *Am. J. Physiol.* 252:E673–E678, 1987) and hepatocytes (Seglen, *J. Toxicol. Environ. Health,* 5:551–560, 1979) are known in the art. Stem cells can also be isolated, and include CD34+ cells, non-human species hematopoietic stem cell equivalents (Heimfeld et al., *Curr. Top. Microbiol. Immunol.* 177:95–105, 1994 and Spangrude et al. *Blood,* 78:1395–1402, 1991) and embryonic stem cells (Robertson, ibid., 1991). Dendritic cells may isolated, for example, from bone marrow, spleen and skin (Steinman et al., WO 93/20185, O'Doherty et al. *J. Exp. Med.* 178:1067–1078, 1993 and Paglia et al., *J. Exp. Med.* 178:1893–1901, 1993).

The selection of culture medium is determined by the cells to be isolated and is a matter of routine experimental design and within the ordinary skill in the art. At a minimum, culture media contain a carbon source, a nitrogen source, essential amino acids, vitamins and minerals. Media may also contain such components as growth factors or serum, as required. A preferred growth medium for osteoclasts contains $\alpha$-MEM (JRH, Lexena, KS), a modified MEM (Eagle, *Science* 130:432, 1959) without ribonucleosides or deoxyribonucleosides, fetal calf serum fractionated on a lysine sepharose column to remove the plasminogen, L-glutamine and sodium pyruvate. In another embodiment, the growth medium contains $\alpha$-MEM (JRH, Lexena, KS), 15% fetal calf serum, L-glutamine and sodium pyruvate and supports the growth of osteoblasts. Certain cell types, for instance, cells of the hematopoietic lineage may require growth factors, such as granulocyte-macrophage colony-stimulating factor (GM-CSF) for growth and/or differentiation to fully activated cells.

A preferred growth medium for the dendritic cells of the present invention contains $\alpha$-MEM (JRH, Lenexa, KS), a modified MEM (Eagle, *Science* 130:432, 1959) without ribonucleosides or deoxyribonucleosides, but containing 5–15% fetal calf serum, L-glutamine, sodium pyruvate, and granulocyte-macrophage colony stimulating factor (GM-CSF). GM-CSF should be added in concentrations of about 1–2000 U/ml, with a preferred range of 500–1000 U/ml. Other factors known to stimulate growth of dendritic cells may be included in the culture medium. Some factors will have different effects that are dependent upon the stage of differentiation of the cells, which can be monitored by testing for differentiation markers specific for the cell's stage in the differentiation pathway. It is preferred to have GM-CSF present in the medium throughout culturing. Other factors that may be desirable to add to the culture medium include, but are not limited to: granulocyte colony-stimulating factor (G-CSF; preferably at about 25–300 U/ml), monocyte-macrophage colony-stimulating factor (M-CSF; preferably at about 100–1000 U/ml), IL-1 (preferably at about 1–100 LAF units/ml), IL-1 (preferably at about 1–100 LAF units/ml), IL-3 (preferably at about 25–500 U/ml), IL-6 (preferably at about 10–100 ng/ml), stem cell factor (SCF; preferably at about 10–100 ng/ml) and thrombopoietin (TPO; preferably at about 1000–10,000 U/ml). When activated dendritic cells are cultured, the medium will preferably include TNF-$\alpha$ (5–500 U/ml, with a preferred range of about 50 U/ml), IL-4 (0.1–10 ng/ml, preferably 10 ng/ml) and interferon-$\gamma$ (25–500 U/ml, with a preferred range of about 100 U/ml).

The dendritic cell line of the present invention, through the course of continuous culturing, allows for growth and expression of immature dendritic cell functions, possibly through the expression of autocrine stimulatory factors, eliminating the need for addition of some or all exogenous growth factors to the growth medium. Because autocrine stimulatory factors are present in the medium conditioned by the cells of the present invention, this medium may be used to stimulate the growth of other dendritic cells.

Additional methods for selective growth of specific cell types include varying the substrate for cell attachment or selective detachment after exposure to trypsin or collagenase (Polinger, *Exp. Cell Res.* 63:78–82, 1970; Owens et al., *J. Natl. Cancer Instit.,* 53:261–269, 1974; Milo et al., In Vitro 16:20–30, 1980; Lasfargues, "Human Mammary Tumors", in Kruse et al. (eds) *Tissue Culture Methods and Applications*, Academic Press, New York, 1973; Paul, *Cell and Tissue Culture*, Churchill Livingston, Edinburgh, 1975).

Once a clonal population of cells has been established from the component cells of a tissue, at least a portion of the isolated cells from each clone is assayed and analyzed for a set of differentiation markers that are characteristic of the cell-type of interest.

A set of differentiation markers is defined as one or more phenotypic properties that can be identified and are specific to a particular cell type. Differentiation markers are transiently exhibited at various stages of cell lineage. Pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. In one preferred embodiment the set of differentiation markers is selected from the group consisting of tartrate-resistant acid phosphatase (TRAP) and calcitonin receptor (Suda et al., *Endocrine Rev.* 13:66–80, 1992); alkaline phosphatase (ALP) (Murthy et al. *Calcif. Tissue Int.* 39:185–190, 1986), osteocalcin (Rodan et al., *Crit. Rev. Eukaryot. Gene Expr.* 1:85–98, 1991) and parathyroid hormone (PTH) receptor (Aubin et al. *J. of Cell Biol.* 92:452–461, 1982); cardiac myosin isozyme expression, creatine kinase isozyme expression and insulin and insulin-like growth factor receptors I (Wolleben et al. ibid.); myosin isozyme expression and a cardiac specific pattern of creatine kinase isozyme expression (Yaffe et al. *Develop. Biol.* 15:33–50, 1967 and Richler et al. *Develop. Biol.* 23:1–22, 1970); myosin isozyme expression and a muscle specific pattern of creatine kinase isozyme expression (I and II) (Yaffe et al. *Develop. Biol.* 11:300–317, 1965; Yaffe et al. *Develop. Biol.* 15:33–50, 1967 and Richler et al. *Develop. Biol.* 23:1–22, 1970); aggrecan (Doege et al. *J. Biol. Chem.* 266:894–902, 1991) and collagen Type IIB (Sandell et al. *J. Cell Biol.* 114:1307–1319, 1991); mpl receptor (Souyri et al., *Cell* 63: 1137–1147, 1990) and acetyl choline esterase (Ravid et al., *J. Cell. Biol.* 123: 1545–1553, 1993); insulin (Powers et al., *Diabetes* 39: 406–414, 1990); glucagon and glucagon-like polypeptide (Lacy et al. ibid., Gotoh et al. ibid. and Hamaguchi et al. *Diabetes* 40:842–849, 1991); somatostatin (Williams et al. Somatostatin and Pancreatic Polypeptide in *International Textbook of Diabetes Mellitus*, Alberti et al., eds., 1992); triglyceride and perilipin (Greenberg et al. *J. Biol. Chem.* 266(17):11341–11346, 1991 and Greenberg et al. *Proc. Natl. Acad. Sci.* 90(24):12035–12039, 1993); Ly-6C and Mac-1 (McCormack et al. *J. Immunol.* 151:6389–6398, 1993 and Gordon et al. *Current Opin. in Immunol.* 4(25):25–32, 1992) and non-specific esterase (NSE; Yam et al., *Amer. J. Clin. Path.* 55:283, 1971); and albumin, liver-specific glucokinase, liver-specific pyruvate kinase and the liver isozyme of glycogen synthase (Miller et al. *J. Biol. Chem.* 261:785–790, 1986 and Magnuson, Diabetes 39: 523–527, 1990), and all combinations thereof.

Immature osteoclast lineage cells are characterized by differentiation markers including Mac-1 expression, TRAP and nonspecific esterase expression, and combinations thereof. Mature osteoclast cells are characterized by a set of differentiation markers including TRAP, calcitonin receptor expression and bone resorptive activity identified in the same cell or clonal population of cells. ALP, osteocalcin expression, PTH-induced cAMP expression and bone mineralization capacity identified together in a cell or clonal population of cells are markers of differentiation for osteoblasts. Cardiac myosin isozyme expression and the cardiac specific pattern of creatine kinase isozyme expression when identified together are markers for cardiac muscles cells; myosin isozyme expression and a muscle-specific pattern of creatine kinase isozyme expression when identified in a cell or clonal population are markers for skeletal muscle cells; aggrecan and collagen Type IIB identified together are markers for chondrocytes; mpl receptor and acetyl choline esterase are markers for megakaryocytes; insulin production is a marker of differentiation for pancreatic $\beta$-cells; glucagon and glucagon-like polypeptide are markers for pancreatic $\alpha$-cells; somatostatin is a marker for pancreatic $\beta$-cells; triglyceride and perilipin are markers for adipocytes; NSE and Mac-1 are markers of differentiation for monocytic lineage cells that include macrophage and osteoclast precursor cells; and albumin, liver-specific glucokinase, liver-specific pyruvate kinase and the liver isozyme of glycogen synthase are markers for hepatocytes.

Differentiation markers used for identifying dendritic cells include: Mac-1, F4/80, Fc RII/III receptor (FcR), MHC class I, MHC class II, B7-1, B7-2, ICAM-1, CD44, N418, and NLDC-145.

In immature dendritic cells, F4/80 (Lee et al. *J. Exp. Med.* 161:475, 1985) and FcR (Unkeless, *J. Exp. Med.* 150:580, 1979) are detectable, but at levels lower than seen in a phenotypically macrophage cell using monoclonal antibodies that bind F4/80 (Caltag, San Fransisco, Calif.) and 2.4G2 for FcR (PharMingen, San Diego, Calif.); MHC class I is detectable using the monoclonal antibody EH144.3 (Geier et al., *J. Immunol.* 137:1239, 1986); MHC class II is detectable only at low levels using the monoclonal antibody AF6-120.1 (PharMingen); B7-1 and B7-2 are detectable at low levels (Nabavi et al., *Nature* 360:266, 1992 and Hathcock et al., *Science* 262:905, 1993, respectively), using monoclonal antibodies IG10 (PharMingen) and GL1 (PharMingen); ICAM-1 (Rothlein et al., *J. Immunol.* 137:1270, 1986) using monoclonal antibody 3E2 (PharMingen) and CD44 (Lesley et al., *Immunogenetics* 15:313, 1982) using monoclonal antibody IM7 (PharMingen); are detectable at high levels, and at least one of the dendritic cell markers CD11c (Metaly et al., *J. Exp. Med.* 171:1753, 1990) using the monoclonal antibody N418, or DC-205 (Kraal et al., *J. Exp. Med.* 163:981, 1986) using the monoclonal antibodies NLDC-145 (Accurate Chem. and Scientific, Westbury, N.Y.) and 33D1 (Nussenzweig et al., *Proc. Natl. Acad. Sci. USA.* 79:161, 1982) should be detectable. The skilled practitioner would recognize that not all of these differentiation markers may be present and that expression levels may vary.

In activated dendritic cells, high levels of MHC class II are detectable, B7-2 and ICAM-1 are expressed at higher levels, and F4/80 is expressed at lower levels than seen in immature dendritic cells.

Identification of a set of differentiation markers is dependent upon the specific marker(s). For example, TRAP (Janckila et al. *Am. J. Clin. Pathol.* 70:45, 1978, incorporated herein by reference), ALP (Goldberg et al. *Nature* 189:297, 1962, incorporated herein by reference) and NSE (Yam et al., ibid. and Brown, B. in *Hematology: Principles and Procedures:*127–130, Lea and Febiger, Philadelphia, 1984, both incorporated herein by reference) activities are identified by cells metabolizing a stain, whereas insulin, glucagon and somatostatin can be identified using immunocytochemistry where protein expression is detected using labeled antibodies (Radvanyi et al., *Mol. Cell. Biol.* 13: 4223–4233, 1993, incorporated herein by reference); calcitonin and PTH receptors can be identified by binding assays using a radiolabeled ligand and assays for cAMP (Aubin et al., *J. Cell Biol.* 92: 452–461, 1982 and Nicholson et al., *J. Clin. Invest.* 78: 355–360, 1986, both incorporated herein by reference); and Mac-1 is identified using conjugated antibodies against the cell-surface antigen (Springer et al. *Eur. J. Immunol.* 9:301–306, 1979, incorporated herein by reference).

Analyses of the cell's surface using monoclonal antibodies are made using a FACScan flow cytometer. For dendritic cell analysis, see, for example, Fink et al., *J. Exp. Med.* 176:1733, 1992 and Crowley et al., *Cellular Immunol.* 118:108–125, 1989. Briefly, the cells are either stained with the monoclonal antibodies directly conjugated to fluorochromes or with unconjugated primary antibody and subsequently stained with commercially available secondary antibodies conjugated to fluorochromes. The stained cells are analyzed using a FACScan (Becton Dickinson, Mountain View, Calif.) using LYSYS II or Cell Quest software (Becton Dickinson).

Identification of activated dendritic cells is confirmed by the cells' ability to stimulate the proliferation of allogeneic T cells in a MLR. Briefly, activated dendritic cells are incubated with allogeneic T cells in a 96-well microtiter dish (American Scientific Products, Chicago, Ill.). Stimulation of the T cells to proliferate is measured by incorporation of $^3$H-thymidine. It is preferred to expose the dendritic cells of the present invention to irradiation to slow the proliferation of the dendritic cells and reduce background in the assay caused by incorporation of $^3$H-thymidine by the dendritic cells.

In addition, Mac-1 is a marker of differentiation for monocytic lineage cells that include dendritic cells, macrophage and osteoclast precursor cells (MacCormack et al., *J. Immunol.* 151:6389–6398, 1993, and Gordon et al., *Current Opin. in Immunol.* 4(25):25–32, 1992). Thus, the Mac-1 marker may be indicative of a dendritic cell precursor. The cell line of the present invention expresses Mac-1, but at levels lower than expected for a typical macrophage cell.

After a subset of cells expressing a set of markers of interest is identified, a portion of the subset is passaged for at least 80 cell generations, preferably 100 cell generations, to establish that the cells are immortalized. Cells not used to establish that the cell line is immortal and can be passaged for the requisite number of cell generations, may be stored for later use using conventional methods well known to those ordinarily skilled in the art. For example, cells may be frozen in growth medium or serum with 15% dimethylsulfoxide (DMSO) added at a temperature of at least −80° C. or lower, preferably −135° C.

Immortalized cells can be stimulated to differentiate and to provide differentiated cells such as osteoblasts, osteoclasts, pancreatic α-cells, pancreatic β-cells, pancreatic δ-cells, adipocytes, macrophages, chondrocytes, dendritic cells and hepatocytes. Differentiation is induced by exposing the undifferentiated stem cells or precursor cells to factors that are specific to a particular cell type. For example, osteoclasts are stimulated to differentiate by exposure to vitamin D and dexamethasone. Osteoblasts are induced to differentiate by exposure to retinoic acid, TGF-α or bone morphogenic proteins (BMP).

Immortalized precursor and immature dendritic cells can be stimulated to differentiate and to provide activated dendritic cells. Differentiation is induced by exposing the undifferentiated stem cells, precursor cells or immature dendritic cells to factors that are specific to a cell's stage in the differentiation pathway. For example, dendritic cells can be exposed to GM-CSF, TNF-α and/or interferon- (Scheicher et al., *J. Immunol. Meth.* 154:253, 1992; Caux et al., *Nature* 360:258–261, 1992; Reid et al., *J. Immunol.* 149:2681–2688, 1992; Lutz et al., *J. Immunol. Meth.* 174:269–279, 1994; Knight et al., *J. Invest. Dermatol.* 99:33S–38S, 1992; and Aiello et al., *J. Immunol.* 144:2572–2581, 1990) to induce differentiation in dendritic cells from immature cells to activated dendritic cells.

Once an immortalized cell line has been established, genetic material from the cells may be used to construct cDNA libraries. Methods for preparing cDNA libraries are well known in the art. See, for example, Sambrook et al. *Molecular Cloning: A Laboratory Manual*, 2nd ed., Cold Spring Harbor Laboratory Press, Cold Spring Harbor, N.Y., 1989 and Ausabel et al., eds. *Current Protocols in Molecular Biology*, John Wiley and Sons, Inc. New York, 1987. By selecting cells at various stages of differentiation the biological functions that are associated with a specific stage in the differentiation pathway may be identified once a cDNA library is prepared from that cell's mRNA.

The libraries may be used to clone novel factors produced by specific cell types that include differentiation factors, growth hormones and other cytokines. For example, osteoblasts can be used to isolate factors that are involved in osteoclast regulation, fracture repair, calcium homeostasis, mineralization and extracellular matrix deposition.

Cells prepared by the methods of the present invention may also be used to prepare a protein library. A protein library is complementary to the cDNA library. Amino acid sequence information obtained from the protein library enables rapid isolation of cDNAs encoding proteins of interest. The use of protein sequence data to design primers for DNA isolation eliminates problems arising in conventional library preparation methods due to relative mRNA abundance. Coupling of protein and cDNA libraries also facilitates the targeted cloning of sequences of particular interest. A protein library is prepared by extracting protein (total proteins or fractions of interest) from cells according to known methods, then separating the proteins by two-dimensional gel electrophoresis. Isolated proteins are then subjected to in situ tryptic digestion followed by separation by micro-bore HPLC. The separated fragments are then analyzed by mass spectrometry. The resulting mass profile is searched against a protein sequence data base to infer protein identity. Unidentified peptides can be sequenced by Edman degradation. The resulting cDNA and protein libraries are valuable sources of new proteins and the sequences encoding them.

The cells of the present invention may also be used for screening agonists and antagonists of compounds and factors that affect the various metabolic pathways of a specific cell. In general, a compound being tested is contacted with a cell line, optionally, in the presence of other agents known to promote or inhibit the metabolic pathway or phenotype of interest, and phenotypic and metabolic changes are monitored in comparison with a control in which the compound being tested is absent. For example, cells of the osteoclast lineage may be used to screen for molecules that inhibit osteoclast growth or differentiation or inhibit bone resorption itself. In addition, the cells of the present invention may be used to generate antibodies for cell-specific proteins, elucidate the interactions between cell types and cell matrix components and may be used for expressing foreign genes. For example, antibodies to cell-surface markers may be generated and used to purify a subpopulation from a heterogenous population of cells using a cell sorting system. Using membrane fragments from cells of the present invention, monoclonal antibodies are produced according to methods known in the art (Kohler et al. *Nature* 256: 495, 1975; *Eur. J. Immunol.* 6: 511–519, 1976) and Hurrell, J. G. R., ed., *Monoclonal Hybridoma Antibodies: Techniques and Applications*, CRC Press Inc., Boca Raton, Fla., 1982) and screened using a variety of cell lines to identify antibodies that display cell specificity. In addition, cell specific monoclonal antibodies can be used to purify cell-surface markers and identify their function. Stem cells and precursor cells can be marked, for example, using β-galactosidase, and their ontogeny followed in heterogenous cell and nutrient environments.

Because dendritic cells can take up, process and present exogenous antigen (including proteins, glycoproteins and peptides), these cells are valuable tools that can be used to identify dominant epitopes of a particular antigen. Such epitope mapping can be attempted by repeated testing with large numbers of defined synthetic peptides, but this process is inefficient, tedious, and not necessarily a mimic of natural antigen processing by antigen presenting cells. The dendritic cells described and claimed herein will naturally process and present exogenous protein, permitting epitope mapping studies that better mimic the in vivo, natural process. At present, the only means available for epitope mapping of naturally processed antigen are EBV-transformed B cells (which are inefficient at taking up (i.e., endocytosing) and processing proteins, and are limited to peptide processing and presentation) and peripheral blood mononuclear cells (PBMNs; a heterogeneous population including B and T lymphocytes, monocytes and dendritic cells).

Moreover, the dendritic cells herein can be used to stimulate naive T cells, as well as primed T cells. This characteristic is unique to dendritic cells, and thus is not available through use of EBV-transformed B cells, for instance.

The dendritic cells of the present invention can be advantageously used in antigen-specific lymphocyte activation assays. To generate activated dendritic cells, it is preferred that activators be incubated with immature dendritic cells for about 1 to 48 hours, most preferably 3 hours.

The dendritic cells are activated to induce expression of MHC class II molecules on the cell surface, making these mature dendritic cells competent for antigen processing and presentation. These activated cells (i.e., stimulators) are then exposed to antigen for a time sufficient for antigen presentation. One skilled in the art would recognize that the time required for endocytosis, processing and presentation of antigen is dependent upon the proteinaceous antigen being used for this purpose. Methods for measuring antigen uptake and presentation are known in the art. For example, dendritic cells can be incubated with a soluble protein antigen (e.g., ovalbumin or conalbumin) for 3–24 hours then washed to remove exogenous antigen.

These antigen-presenting stimulator cells are then mixed with responder cells, preferably naive or primed T lymphocytes. After an approximately 72 hour incubation (for primed T lymphocytes) or approximately 4–7 day period (for naive T lymphocytes), the activation of T cells in response to the processed and presented antigen is measured. In a preferred embodiment, T cell activation is determined by measuring T cell proliferation using $^3$H-thymidine uptake (Crowley et al., *J. Immunol. Meth.* 133:55–66, 1990). The responder cells in this regard can be PBMN cells, cultured T cells, established T cell lines or hybridomas. Responder cell activation can be measured by the production of cytokines, such as IL-2, or by determining T cell-specific activation markers. Cytokine production can be assayed by the testing the ability of the stimulator+ responder cell culture supernatant to stimulate growth of cytokine-dependent cells. T cell-specific activation markers may be detected using antibodies specific for such markers.

For T cell proliferation assays, it is preferred to inhibit the proliferation of dendritic cells prior to mixing with T responder cells. This inhibition may be achieved by exposure to gamma irradiation or to an anti-mitotic agent, such as mitomycin C.

Alternatively, activated dendritic cells can be used to induce non-responsiveness in T lymphocytes. In addition to MHC class II recognition, T cell activation requires co-receptors on the antigen-presenting cell (APC; e.g., dendritic cell) that have been stimulated with co-stimulatory molecules. By blocking or eliminating stimulation of such co-receptors (for instance, by blocking with anti-receptor or anti-ligand antibodies, or by "knocking out" the gene(s) encoding such receptors), presentation of antigen by co-receptor-deficient dendritic cells can be used to render T lymphocytes non-responsive to antigen.

For some applications, it is preferable to genetically manipulate the dendritic cells so that they overexpress MHC class II molecules at their surface.

In yet another embodiment, the dendritic cells of the present invention can be transfected with a polynucleotide encoding a heterologous protein involved in antigen presentation to responder cells. In a preferred embodiment, the dendritic cells are transfected with a polynucleotide encoding a selected MHC class II molecule of interest. Any MHC class II molecule of mammalian origin may be used in this regard, with MHC class II molecules associated with a particular disease preferred. Human MHC class II molecules associated with autoimmune diseases, and especially those associated with diabetes (e.g., DR4, DR3, DQ2 and DQ8), are particularly preferred. It is also preferred that endogenous MHC class II molecules are blocked or eliminated, thereby providing an APC cell that expresses or overexpresses only one type of MHC class II on its surface. Blocking may be achieved using antibodies directed against endogenous MHC class II; however, heterodimers of endogenous and heterologous MHC class II chains may not be blocked and may provide anomalous results. More preferably, the coding region for endogenous MHC class II is eliminated, such as by gene disruption by means of homologous recombination.

For instance, dendritic cells of the present invention can be transfected with a polynucleotide encoding human DR4. The genes encoding endogenous MHC class II molecules (i.e., I-A and I-E) are eliminated by homologous recombination, so that only human DR4 can be expressed by the transfected cells. These DR4-expressing dendritic cells are activated to induce cell surface expression of DR4, and exposed to exogenous glutamic acid decarboxylase (GAD) antigen. After a time sufficient for natural antigen endocytosis, processing and presentation, the antigen-presenting, transfected cells are combined with responder cells. In a preferred embodiment, these responder cells are PBMN cells obtained from patients with diabetes.

At this point, the responder T cells can be selectively amplified and/or stimulated, thereby producing a subset of T cells that are specific for GAD and restricted by the DR4 allele. For instance, DR4-expressing T cells may be selected by flow cytometry, and particularly by fluorescence activated cell sorting. This subset of DR4-restricted T cells can be maintained by repetitive stimulation with DR4-expressing dendritic cells presenting GAD antigen. Alternatively, T cell clones can be established from this T cell subset. Further, this subset of T cells can be used to map GAD epitopes, and to define relevant GAD peptides that are presented by DR4 on the APC.

Alternatively, MHC class II molecules identified in model systems of autoimmune disease may be further studied by transfecting a polypeptide encoding the disease-associated MHC class II molecules into the dendritic cells. For instance, a polynucleotide encoding I-$A^{g7}$ MHC class II molecules of NOD mice, a model system for insulin-dependent diabetes mellitus (IDDM), can be transfected into the dendritic cells. Such I-$A^{g7}$ expressing dendritic cell may be a useful research reagent, particularly because this APC is homogeneous and provides "off the shelf" availability. Further, an I-$A^{g7}$ expressing dendritic cell can be used in conjunction with dendritic cells transfected with human diabetes-related MHC class II molecules, to better identify the strengths and limitations of the model system.

The dendritic cells of the present invention also provide a stable, reproducible, relatively homogeneous population of cells that can be cultured and obtained in significant numbers. The low frequency of dendritic cells in mononuclear cell preparations has prevented extensive molecular, biochemical and physiological study of this unique type of APC. The claimed cell line permits, for the first time, an examination of molecules, including polynucleotides and proteins, that may be uniquely expressed in dendritic cells. More particularly, these dendritic cells will permit identification and analyses of genes, proteins, metabolic and proteolytic processes, as well as other molecules and processes, that enable dendritic cells to be such potent APCs. The molecules and processes involved in endocytosis are of interest, since dendritic cells are particularly effective at taking up exogenous antigen. The molecules and processes involved in antigen processing are also of interest, since dendritic cells are uniquely able to process exogenous antigen for presentation. Related cell components and their interaction with molecules and processes involved in antigen uptake, processing and presentation can also be dissected. For instance, these dendritic cells can be used to examine one or a set of co-stimulatory molecules, and to determine whether unique properties or interactions of these co-stimulatory molecules contribute to the superior antigen processing and presenting characteristics of dendritic cells. Likewise, other components that play a role in cellular immunology (for instance, DM genes and invariant chain) may be analyzed in this setting. Furthermore, this homogeneous dendritic cell line can be used as an immunogen to identify lineage-specific markers for dendritic cells.

Compounds identified as therapeutic agents by screening with the cell lines of the invention are formulated for therapeutic use as pharmaceutical compositions. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The invention is illustrated by the following, non-limiting examples.

EXAMPLE I

Preparation of an Osteoclast Precursor Cell Line
A. Harvesting cells from p53 knockout mice Three male p53 knockout mice homozygous were purchased from GenPharm (Mountain View, Calif.). The mice were approximately five weeks old. The mice were sacrificed by cervical dislocation and swabbed with ethanol. The skin was removed from the animals and the femurs dissected out. In a sterile environment, the soft tissue was removed from the bone and the cortical ends cut off, leaving the long bone portion of the femur. Bone marrow was removed from the femur long bone by forcefully expressing the marrow from the medullary cavity using a 26 gauge needle and 10 cc syringe.

The bone marrow was placed in a centrifuge tube in several milliliters of growth medium (Table 1) and spun in a Beckman TJ-6 centrifuge (Beckman Instruments, Palo Alto, Calif.) at 3,000 rpm for 5 minutes. The cells were resuspended in growth medium, counted and plated at a density of $1 \times 10^6$ cells/ml in multiple 10-cm culture dishes (American Scientific Products, Chicago, Ill.).

TABLE 1

| |
| --- |
| 500 ml α-MEM (GIBCO BRL, Gaithersburg, MD) |
| 10% fetal calf serum (HyClone, Logan, Utah) |
| 1mM sodium pyruvate (Irvine, Santa Ana, CA.) |
| 0.29 mg/ml L-glutamine (Hazelton, Lenexa, KS.) |

The cells were allowed to attach and grow for 3 days at 37° C. in 5% $CO_2$. After the incubation period, suspension cells were removed by pipetting off spent medium and removing any non-adherent cells. The cells were incubated for approximately one week or until each clone had formed a sizable colony. Each colony was subcloned by harvesting the cells using Sigma NONENZYMATIC ASSOCIATION AGENT (Sigma, St. Louis, Mo.) and plated in duplicate culture dishes, one for maintaining the cell line, and the other for further characterization. One cell line, designated OC10A, was found to have characteristics of osteoclasts when cultured in conditions that promoted differentiation.
B. Characterization of osteoclast phenotype by calcitonin binding assay The subcloned cells were plated at a density of $5 \times 10^4$ cells/well on an 8-chamber slide (Nunc, Naperville, Ill.) and allowed to grow for 1 week to 10 days at 37° C. and 5% $CO_2$ in 500 μl of growth medium with $10^{-8}$M 1α, 25-dihydroxycholecaliferol and $10^{-7}$M dexamethasone added to promote differentiation. The medium was removed, and the cells were washed in PBS. Three hundred microliters of binding medium (RPMI (Fred Hutchinson Cancer Research Center, Seattle, Wash.) and 0.1% BSA) was added to each well. Three hundred microliters of binding medium containing 0.2 nM radiolabeled $^{125}$I salmon calcitonin with a specific activity of approximately 1000 Ci/mmole (Peninsula, Belmont, Calif.) were added to half the wells, and 300 l of binding medium containing 0.2 nM $^{125}$I salmon calcitonin and 1 μM unlabeled salmon calcitonin were added to the remaining wells. The slides were incubated for 1.5 hours at room temperature, then rinsed 3 times with PBS to remove unincorporated radioactivity. The slides were immediately prepared for TRAP staining.

C. Characterization of osteoclast phenotype by TRAP staining

Osteoclasts express an acid phosphatase that is tartrate resistant (TRAP). TRAP staining detects cells that are tartrate resistant by formation of an insoluble red stain. Slides that had been treated for calcitonin receptor analysis (example IB) were fixed by adding 100 μl of a solution containing 2.5% glutaraldehyde and 3.5% formaldehyde in PBS for 10 minutes. After the glutaraldehyde/formaldehyde solution was removed, 100 l of a 1:1 acetone/ethanol solution was added for 1 minute. An Acid Phosphatase, Leukocyte kit (Sigma, St. Louis, Mo.) was used to prepare a substrate solution containing 45 ml of deionized water at 37° C. 1.0 ml of Diazotized Fast Garnet GBC solution (0.5 ml Fast Garnet GBC Base solution and 0.5 ml sodium nitrite solution), 0.5 ml Naphthol AS-BI Phosphate solution, 2.0 ml Acetate solution and 1.0 ml tartrate solution according to the manufacturer's specifications. Approximately 100 μl of the substrate solution was added to each well. The plates were incubated at 37° C. for 30–60 minutes. The stain was removed and the plates were washed gently with tap water. The slides were examined microscopically for TRAP positive cells. After examination the slides were dipped in Kodak NTB3 emulsion (Kodak, Rochester, N.Y.) and allowed to air dry. The slides were placed at 4° C. for 12 days in the dark and developed in Kodak D19 developer (Kodak). After being developed, the slides were fixed in RAPID FIX (Kodak) for 5 minutes. A differentiated subpopulation of clone OC-10 was found to express the calcitonin receptor and tartrate-resistant acid phosphatase.

D. NSE Staining for Identification of Monocyte/Macrophage Lineage

The NSE assay uses specific esterase substrates in defined reaction conditions to distinguish granulocytes from monocytes. Cells of the monocyte lineage include macrophages and osteoclasts. Bone marrow cultures are incubated with alpha-naphthyl acetate in the presence of a stable diazonium salt. Enzymatic hydrolysis of ester linkages liberates free napthol compounds. The napthol compounds couple with the diazonium salt, forming highly colored deposits at the sites of enzyme activity.

Cells were plated at $5 \times 10^4$ cells/well on an 8-chamber slide (Nunc). The cells were affixed to the slides in Citrate-Acetone-Methanol Fixative for 1 minute at room temperature. The fixative was prepared using 18 ml of citrate dilute solution (0.383M citrate buffer pH 5.4 diluted 1 part citrate buffer to 9 parts deionized water pH 5.4), 27 ml ACS grand acetone and 5 ml methanol. After fixation, the slides were washed thoroughly in deionized water and air dried for at least 20 minutes. A capsule of FAST BLUE RR SALT (Sigma, St. Louis, Mo.) was added to 50 ml of TRIZMAL 7.6 Dilute Buffer Solution (Sigma) in a Coplin jar. One part TRIZMAL 7.6 buffer concentrate is diluted with 9 parts deionized water to make the dilute solution. When the salt was dissolved, 2 ml of alpha-Naphthyl Acetate solution (Sigma) was added and stirred for 15–20 seconds. Specimen slides were added to the jar and incubated for 30 minutes at 37° C. The slides were removed from the stain and washed for 3 minutes in deionized water, air dried and examined microscopically. NSE positive cells were seen in OC10A cultures, with and without the addition of 1α 25-dihydroxycholecalciferol, indicating the presence of cells of the monocytic lineage.

E. Identification of the Mac-1 Antigen

Mac-1 is a cell surface antigen expressed by monocytes, granulocytes and macrophages, but not by mature osteoclasts. Mac-1 positive cells were identified by using a rat monoclonal antibody to Mac-1 (Boehringer Mannheim, Indianapolis, Ind.).

Cells were prepared on 8 chamber slides as discussed in the previous examples. The wells were rinsed in PBS with 1 mg/ml BSA added and fixed in Z FIX (Anatech Ltd., Battle Creek, Mich.) for 10 minutes. After fixing the wells were rinsed in PBS/BSA solution. The chambers were removed, retaining the gaskets on the slides. The anti-Mac-1 antibody was diluted 1:20 in the PBS/BSA solution, and 25 l/well of the antibody solution was added to each well and incubated for 45 minutes at room temperature. After incubation, the wells were rinsed three times in the PBS/BSA solution. Twenty-five microliters of goat FITC-Anti-rat IgG (Boehringer Mannheim) diluted 1:50 in PBS/BSA solution was added to each well and incubated for 45 minutes at room temperature in the dark. The wells were rinsed three times in PBS/BSA solution and a final rinse in water was done. The gaskets were removed and a coverslip was mounted on the slide using mounting solution prepared using 9 parts of 2% 1,4 diazobicyclo(2,2,2)-octane in glycerol (Sigma, St. Louis, Mo.) that was dissolved at 70 and 1 part 0.2M Tris-HCL and 0.02% $NaN_3$ (pH 7.5) to prevent fading. Cultures of OC10 A that had been treated with $10^{-8}$M 1α, 25-dihydroxycholecalciferol and $10^{-7}$M dexamethasone were found contain Mac-1 positive cells.

F. Characterization of Bone Resorptive Activity

Bovine cortical bone wafers were cut on a Buehler 11-1180 isomet low speed saw (Buehler, Lake Bluff, Ill.). The slices were measured and sterilized using ethanol and ultraviolet light exposure overnight. The wafer sizes varied between 0.1–0.19 mm. The wafers were rinsed in PBS and stored hydrated in growth medium at 37° C. in 5% $CO_2$. The wafers were placed in 8-chamber slides (Nunc), and cells were plated on the wafers at a density of $5 \times 10^4$ cells/well. The medium was changed every four days. On day 10, the medium was changed to low pH α-MEM with 0.7 g/L $NaHCO_3$, $10^{-8}$M 1α,25-dihydroxycholecalciferol and $10^{-7}$M dexamethasone added. On day 12 the medium was removed, trypsin/EDTA solution was added overnight, and the wafers were sonicated to remove the cells from the wafers. The wafers were rinsed in PBS and stained with 1% Toluidine Blue and 1% sodium borate for 1 minute. The excess stain was removed by washing with PBS followed by water. The wafers were viewed under an inverted scope at 10× magnification for quantitation of resorption pits using the Optimas Image Analysis program (Bioscan, Edmonds, Wash.). Results of the microscopy demonstrate that OC10A cultures resorb bone.

EXAMPLE II

Preparation of an Osteoblast Cell Line

A. Harvesting cells from calvaria

Calvaria were removed from three p53 knockout mice (see Example IA) and placed in a 10 cc petri dish with 5 to 10 ml of growth medium (Table 1) containing 15% fetal calf serum. The calvaria were rinsed once in growth media. After rinsing, calvaria were placed in a Falcon centrifuge tube (Becton Dickinson Labware, Lincoln Park, N.J.) and minced using scissors. The minced bone was spun in a Beckman TJ-6 centrifuge (Beckman Instruments) at 1000 rpm for 10 minutes at room temperature. The bone was separated from the supernatant, and 3 ml of growth medium with 0.1% Type II collagenase (Sigma) was added to the minced bone pieces. The bone and collagenase mixture was incubated by shaking for 10 minutes at 37° C. After incubation, the supernatant was removed with a pipette, leaving bone pieces behind. The supernatant was placed in a 15 ml conical bottom Falcon centrifuge tube (Becton Dickinson Labware), and 3 ml of fetal calf serum was added to stop the collagenase digestion. The mixture was centrifuged at 1000 rpm for 10 minutes. After centrifugation, the cells were resuspended in 3 ml of growth medium with 15% fetal calf serum added to the medium. The collagenase digestion of the calvarial bone pieces was repeated five times, separating the supernatant from the bone pieces after each digestion. The bone pieces were washed five times in 15 ml of phosphate buffered saline (PBS) with 0.133 g/l calcium chloride-$2H_2O$ and 0.1 g/l magnesium chloride-6 $H_2O$ and then placed in growth medium with 15% fetal calf serum. Cultures containing cells from the serial digestions and bone pieces were placed at 37° C. and 5% $CO_2$ in growth medium. The cells were seen to crawl from the bone pieces after approximately 2–4 days.

The cells were replated at a clonal density of 1 cell/well in a 96-well petri dish containing growth medium. Single colonies were replica plated, with one replicate petri dish of the colony maintained as a cell line and the other used for characterization. Characterization included testing for the presence of alkaline phosphatase, Von Kossa staining (to visualize in vitro and in vivo mineralization), Alizarin Red S staining (to visualize in vitro mineralization), Goldner staining (to visualize in vivo mineralization), PTH induction of cAMP and osteocalcin expression.

B. Expression of Alkaline Phosphatase

Expression of alkaline phosphatase as a marker of osteoblast phenotype was assayed using a diagnostic kit (Sigma, St. Louis, Mo.) according to manufacturer's specifications. Briefly, cells are affixed with a citrate/acetone/formaldehyde fixative (Sigma) to slides and then incubated in a solution containing naphthol AS-MX phosphate. In the presence of phosphatase activity, naphthol AS-MX is liberated and immediately coupled with a diazonium salt, forming an insoluble, visible pigment at the sites of phosphatase activity. Three cell lines, designated 2-29, 2-45 and CCC-4 stained positive for alkaline phosphatase stain red.

C. cAMP induction by PTH

The ability of PTH to induce cAMP production in cell lines 2-29, 2-45 and CCC-4 was measured using a Scintillation Proximity Assay kit (Amersham, Arlington Heights, Ill.) according to the manufacturer's specifications. Briefly, $1 \times 10^5$ cells/well were plated into the wells of a 24-well plate (American Scientific Products, Chicago, Ill.) and grown for 2 days in selection medium. PTH and forskolin were prepared in α-MEM, 10% fetal calf serum and 10M IBMX.

The growth medium was replaced with 200 µl/well of growth medium containing agonist, either PTH (bovine fragment 1-34, Sigma) or forskolin. The cells were incubated with the agonists for 10 minutes at 37 in 5% $CO_2$. Following incubation, 800 ll of boiling water was added to each well. After 15 minutes the supernatants were collected and diluted 1:5 or 1:40 in acetate buffer (cAMP [$^{125}$I] Scintillation Proximity Assay System (Amersham)). Samples were acetylated using triethylamine and acetic anhydride according to the protocol provided by the manufacturer.

A 100 µ/l aliquot of each acetylated sample was combined with 75 1 of $^{125}$I-cAMP, 75 1 anti-succinyl cAMP antisera and 75 1 of donkey anti-rabbit IgG coupled SPA beads (all assay solutions provided in the cAMP [$^{125}$I] Scintillation Proximity Assay System (Amersham)) in a well of a Dynatech MICROLITE 2 plate. The trays were sealed and incubated overnight with continuous shaking on a rotary platform shaker at 200 rpm. The samples were counted in a Packard Top Count Microplate Scintillation Counter (Packard Instrument Co., Meriden, Conn.). A standard curve of 2-128 fmol acetylated cAMP was also run. Total $^{125}$I-cAMP bound and nonspecific binding was also determined.

|  | −PTH | +PTH |  |
|---|---|---|---|
| 2-29 | 54 | 1155 | 22-fold |
| 2-45 | 45 | >8000 | >176-fold |
| CCC-4 | 34 | 1280 | 37-fold |

The results clearly demonstrate that PTH induced cAMP production in cell lines 2-29, 2-45 and CCC-4.

D. Characterization of Bone Mineralization

Mineralization was induced by the addition of 10 mM β-glycerophosphate and 50 µg/ml ascorbic acid to the culture medium. Cells were grown in the supplemented medium for 1–3 weeks. The medium was removed from the cells, and the petri dish was rinsed in PBS. Cells were fixed with Z-FIX (Anatech Ltd.). After fixing, the cells were rinsed three times with distilled water. A solution of five grams of silver nitrate in 100 ml of water was added to the cells at 1 ml/well and placed in the dark for 5 minutes. After incubation, the cells were rinsed three times in distilled water. A solution of 5 g of sodium carbonate, 75 ml distilled water and 25 ml of 38% formaldehyde was added to each well at 1 ml/well for 1 minute. The cells were rinsed 2–3 minutes with tap water. Farmer's Reducer (0.2 ml of 10% sodium thiosulfate, 1.0 ml of 0.1 g/ml potassium ferricyanide, 20 ml of water) was added at 1 ml/well for 1 minute. The cells were rinsed 10 minutes with tap water. Cells were scored visually for silver staining.

Alizarin Red S staining was done by rinsing cells with PBS and fixing the cells with Z-FIX for 10 minutes. The cells were rinsed several times in distilled water. Alizarin Red S stain (Sigma) was prepared at a concentration of 0.2 gr/10 ml PBS and used to stain cells in the culture dishes for 5 minutes. The excess stain was removed by rinsing with distilled water.

The ability of cells to mineralize bone in vivo was measured by placing diffusion chambers in mice. Diffusion chambers (Millipore, Bedford, Mass.) were filled with approximately $5 \times 10^6$ cells/130 µl PBS/chamber. Swiss-webster mice (B&K Universal, Seattle, Wash.) were anesthetized with ketamine and xylazine. Chambers were surgically implanted intraperitoneally and closed using silk interrupted sutures. Skin clips were used to close the skin layer. After 9 weeks mice were sacrificed, diffusion chambers were fixed, processed and embedded in plastic, and histology was performed to measure bone mineralization by Von Kossa staining as described above and Goldner's trichrome stain.

The diffusion chamber samples were prepared by fixing the chambers in 10% neutral buffered formalin (Anatech) for 24 hours at 4° C. The chambers were processed in a BIP 2000 Automatic Tissue Processor (Miles Scientific, Elkhardt, Ind.). The processed chambers were infiltrated at 4° C. with a first solution of 15 ml of 70% methyl methacrylate, 30% n-butyl methacrylate in a scintillation vial placed on an orbital shaker. The chambers were embedded by placing the vials at 4° C. and covered in a solution containing 70% methyl methacrylate, 30% n-butyl methacrylate, 1:20 volume methanol, 3% benzoyl peroxide and 1:600 volume n,n-dimethylaniline and placed under vacuum in a glass desiccator. The process was repeated for a second embedding.

The embedded slides were sectioned on a Reichert-Jung Autocut microtome, and 5 µm sections were mounted on glass slides. The slides were stained using Von Kossa stain and Goldner's trichrome stain. Sections were placed in Mayer's hematoxylin (Sigma) for 1 hour and rinsed in tap water for 1 minute. The sections were covered with 0.25% ammonium hydroxide in water for 45 seconds and rinsed in tap water for 1 minute. The sections were covered with Ponceau/acid fuchsin (prepared using 0.13 g of Ponceau de Xylidine (Sigma), 0.03 g of acid fuchsin, 0.2 ml of glacial acetic acid and 100 ml of distilled water) for 10 minutes, transferred to 1% glacial acetic acid for two rinses, and rinsed once in 0.5% glacial acetic acid. The sections were transferred to phosphomolybdic acid/orange (prepared using 5 g of phosphomolybdic acid, 100 ml of distilled water and 2 g of orange G) for 10 minutes, and rinsed twice with 1% glacial acetic acid and once in 0.5% glacial acetic acid. Sections were placed in light green stain (prepared using 0.3 g of light green stain (Sigma), 0.2 ml of glacial acetic acid and 100 ml of distilled water) for 10 minutes. Sections were rinsed twice in 1% glacial acetic acid, followed by rinses in 70% ethanol and 95% ethanol. The sections were transferred twice into absolute ethanol for 2 minutes, and then transferred three times into xylene for 2 minutes.

The cell lines designated 2-29, 2-45 and CCC-4 all showed detectable mineralization in vitro 5–8 days after the addition of β-glycerophosphate and ascorbic acid. In vivo mineralization was demonstrated for all three cell lines six weeks after implantation of the diffusion chambers.

D. Expression of Osteocalcin

Osteocalcin expression was measured using a radioimmune assay kit from Biomedical Technologies, Inc. (Stoughton, Mass.) according to the manufacturer's specifications. Briefly, media samples were collected from cell lines and prepared either undiluted or diluted 1:5. $^{125}$I osteocalcin is added, followed by goat anti-mouse osteocalcin. The complex was precipitated using donkey anti-goat antibodies and centrifuged. The radioactivity in the resulting pellet was measured on a gamma counter, and osteocalcin secretion was calculated as the ng of osteocalcin present in the medium per well.

| | osteocalcin (ng/well) | |
|---|---|---|
| cell line | −β-glycerophosphate and ascorbic acid | +β-glycerophosphate and ascorbic acid |
| 2-29 | 58 | 1050 |
| 2-45 | 114 | 1775 |
| CCC-4 | 306 | 4800 |

Results clearly demonstrate that in the presence of β-glycerophosphate and ascorbic acid, osteocalcin was secreted in cell lines 2-29, 2-45 and CCC-4.

EXAMPLE III

Osreoblast Cell Line 7F2

A fourth clonal osteoblast cell population, designated cell line 7F2, was isolated from bone marrow as described in Example IA. The 7F2 cell line was stable in αMEM, 10% fetal calf serum media. The cell line expressed a set of differentiation markers characteristic of osteoblast cells, which includes PTH-induced cAMP expression, secretion of osteocalcin, alkaline phosphatase expression, bone mineralization capacity, and secretion of type I collagen. No cells having the visual appearance of adipocytes (i.e., oil red O staining cells) were observed by microscopy.

On treatment of the 7F2 cell line with a cocktail of inducing agents reported to induce preadipocyte cells derived from bone marrow cells (Gimble et al., *J. Cell. Biol.* 50, 73–82 (1992)), expression of osteoblastic differentiation markers ceased, and there was massive appearance of mature adipocytes. The cocktail of agents used to induce this change of phenotype was 50 µM indomethacin, 0.1 mM dexamethasone and 50 µg/ml dexamethasone and cells were plated at 2×10$^7$ cells/well in a microtiter dish. Each of these agents can be used at a range of concentrations within about a factor of 10 or 100 from those indicated, and indomethacin can be used alone. The adipocytes appeared within 7 days of culturing under these conditions. The properties of cell line 7F2 compare with the adipocytes obtained after treatment with the above cocktail of agents as follows:

| | Cell Line 7F2 | Cell Line 7F2 + cocktail |
|---|---|---|
| Oil Red O Staining† | — | +++ |
| PTH-induced cAMP | 21× | 1× |
| forskolin-induced cAMP | 20× | 23× |
| Osteocalcin | 5.2 ng/ml/48 hr | <1 ng/ml/48 hr |
| Alkaline Phosphatase | + (homogeneous) | +/− (heterogeneous) |
| Bone Mineralization | 6.5 mM | 0.4 mM |

In addition to the general uses of immortalized cells discussed above, cell line 7F2 and similar cell lines are useful for screening compounds for activity in promoting or inhibiting conversion of osteoblasts to adipocytes. This utility arises due to an inverse relationship reported between the differentiation of adipocytes and osteogenic cells in vitro (Beresford et al., *J. Cell. Sci.* 102, 341–351 (1992) and correlations between increased volume of marrow adipose tissue and osteoporosis (Meunier et al., *Clin. Orthop. Rel. Res.* 80, 147–154 (1971); Burkhardt et al., *Bone* 8, 157–164 (1987); Minaire et al., *Calcif. Tiss. Int.* 36, 338–340 (1984). These results suggest that conversion of osteoblasts to adipocytes is a factor in the disease of osteoporosis. Cell line 7F2 and similar cells lines can therefore be used in screening items, such as food or drugs, for undesired activity in promoting osteoporosis. The compound being tested is contacted with the cell line, optionally, in the presence of other agent(s) promoting conversion to adipocytes, and conversion to adipocytes is monitored relative to a control mixture in which the compound being tested is absent. The cell line can also be used to screen compounds for potential activity in inhibiting osteoporosis. In this case, the cell line is contacted with a compound being tested and an agent effective to induce conversion of the cell line to adipocytes and conversion of the cell line to adipocytes is measured in comparison with a control in which the compound being tested is absent. Conversion can be measured either by the rate of appearance of adipocytes as a function of time or the proportion of osteoblasts that have converted after conversion has reached steady state.

EXAMPLE IV

Preparation of Dendritic Cells

The isolated cell line designated JAWS II, and deposited at the American Type Culture Collection (12301 Parklawn Drive, Rockville, Md.), was identified as a monocytic lineage cell expressing dendritic cell phenotype according to the following methods:

A. Mac-1 Antigen

Cells were prepared as described in Example I E for assay of the JAWS II cells for the presence of a rat monoclonal antibody to Mac-1 on the cell surface. Results showed that cultures of JAWS II expressed Mac-1 on their cell surface.

B. Calcitonin binding assay

The JAWS II cell line was assayed for the presence of the calcitonin receptor by preparing the JAWS II cells as described in Example I B. The slides were immediately prepared for TRAP staining, as described previously.

C. TRAP staining

Expression of a tartrate resistant form of acid phosphatase (TRAP) on dendritic cells was assayed. Slides that had been treated for calcitonin receptor analysis (Example IV B) were prepared as described in Example I C. An analyzed subpopulation of the JAWS II cell line did not express the calcitonin receptor, and was positive for expression of tartrate-resistant acid phosphatase.

D. NSE Staining for Identification of Monocyte/Macrophage Lineage

The Nonspecific Esterase (NSE) assay uses specific esterase substrates in defined reaction conditions to distinguish granulocytes from monocytes. Dendritic cells come from the monocyte lineage. Cells were prepared as described in Example I D. NSE positive cells were seen in JAWS II cultures, with and without the addition of 1,α25-dihydroxycholecalciferol, indicating the presence of cells of the monocytic lineage.

E. Characterization of Bone Resorptive Activity

Bovine cortical bone wafers were prepared as described in Example I F. The wafers were viewed under an inverted scope at 10x magnification for quantitation of resorption pits using the Optimas Image Analysis program (Bioscan, Edmonds, Wash.). Results of the microscopy demonstrate that JAWS II cultures did not resorb bone.

F. FACScan Analysis of the Cell Surface

Analyses of the cell surface proteins of JAWS II was made using FACScan (Becton Dickinson) using LYSYS II or Cell Quest software (Becton Dickinson) according the manufacturer's specifications.

Approximately $10^6$ cells were incubated at 4 for 15–20 minutes in BSS-BSA (Hank's buffered salts solution which contains 0.0345% sodium bicarbonate, 5 mM HEPES, 1% bovine serum albumin) containing primary antibody. The primary antibody solution was removed, and the cells were washed with BSS-BSA and resuspended in phosphate-buffered saline (PBS). If the primary antibody was not conjugated with a fluorochrome, then the washed cells were similarly incubated at 4° C. with a fluorochrome-conjugated secondary antibody before washing and resuspension in PBS.

The results, shown in Table 1, demonstrate that JAWS II has cell-surface markers associated with the phenotype of an immature dendritic cell, and when induced with combinations IFN -γ, TNF-α and IL-4, the cells exhibit markers associated with activated dendritic cells. The splenic dendritic cells are from C57Bl/6 mice (Jackson Labs) and were isolated (as activated dendritic cells) using preferential adherence and detachment to plastic, as described by Swiggard et al. (Curr. Protocols Immunol. 3.7.1–3.7.11, 1992).

TABLE 1

| | Surface proteins/antigens | (mAb) | JAWS II | Splenic DC* (B6 mice) |
|---|---|---|---|---|
| 1 | MHC class I | EH144.13 | High | High |
| 2 | MHC class II | AF6-120.1 | negative/low | High |
| 3 | MHC Class II + IFN-gamma | | High | NT |
| 4 | B7-1/BB1 (CD80) | 1G10 | negative/low/intermed. | negative/low/intermed. |
| 5 | B7-1/BB1 + IFN-gamma | | Decreased | NT |
| 6 | B7-2 (CD86) | GL1 | negative/low/intermed. | low/intermed. |
| 7 | B7-2 + IFN-gamma/TNF-alpha/IL-4 | | Increased (low/intermed. | NT |
| 8 | ICAM-1 (CD54) | 3E2 | Intermed. | High |
| 9 | ICAM-1 + IFN-gamma/TNF-alpha/IL-4 | | High | NT |
| 10 | DC-205 | NLDC-145 | Intermed. | negative/low/intermed. |
| 11 | | | | (Intermed./high in BALB/c DC) |
| 12 | Mac-1 (CD11b) | M1/70- | High | negative/low |
| 13 | Fc-gamma-RII/III receptor | 2.4G2 | High | negative/low |
| 14 | F4/80 | F4/80 | High | Low |
| 15 | F4/80 + IL-4 | | Decreased somewhat | NT |
| 16 | Pgp-1 (CD44) | 1M7 | High | High |
| 17 | HSA (Heat Stable Antigen; CD24) | M1/69 | High | High |
| 18 | B220 (B cell antigen) | RA3-6B2 | negative | negative |
| 19 | Thy1 (T cell antigen) | TS | negative | negative |
| 20 | CD4 (T cell antigen) | RM4-5 | negative | negative |
| 21 | CD8 (T cell antigen) | 53-6.7 | negative | negative |
| 22 | Plastic adherence | | Low | Low |
| 23 | Stimulation of allo-MLR | | Low | Very High |
| 24 | allo-MLR + IFN-gamma/TNF-alpha/IL-4 | | High | NT |

NT = not tested

G. Mixed Lymphocyte Reaction (MLR)

i. Preparation of stimulator cells (dendritic cells)

JAWS II cells were grown to high density ($1-2 \times 10^6$ cells/ml) in α-MEM (Minimal Essential Medium, alpha-modification, containing 10% fetal bovine serum (FBS), 1 mM sodium pyruvate, 4 mM glutamine)+5 ng/ml murine GM-CSF. Additional cytokines used to activate the cells included interferon-γ (100 U/ml), tumor necrosis factor-α (10 ng/ml), and interleukin-4 (10 ng/ml). The culture supernatant containing the nonadherent cells was pooled with adherent cells removed by washing with Versene and the cells were resuspended at $3 \times 10^5$ cells/ml in RPMI-1640 medium (containing 10% FBS, 10 mM HEPES, 4 mM glutamine, $5.7 \times 10^{-5}$M 2-mercaptoethanol, 50μg/ml gentamycin, 100 U/ml penicillin, 100 μg/ml streptomycin).

Splenic dendritic cells were isolated by the method of Swiggard et al. (Curr. Protocols Immunol. 3.7.1–3.7.11, 1992) from spleens of C57Bl/6 and BALB/c mice. Briefly, single cell suspensions of spleen cells were generated by digestion with collagenase and a low density fractionation. The low density fraction was obtained by centrifugation of the cells through a low density solution (refractive index of approximately 1.364) of bovine serum albumin (BSA) in phosphate-buffered saline (PBS) onto a high density cushion (refractive index of approximately 1.385) of BSA in PBS and contained primarily dendritic cells, macrophages, and some B cells. Cells were resuspended at 37 in RPMI medium at $1 \times 10^7$ cells/ml and 4 ml of the suspension was plated per 60 mm tissue culture plate. After a 90 minute incubation at 37° C., nonadherent cells were gently removed, adherent cells were washed with RPMI, and incubated in RPMI for an additional 30–60 min. Nonadherent cells were again removed and adherent cells gently washed with RPMI and incubated in RPMI for 12–20 hours at 37° C. Splenic dendritic cells detached during the final incubation and were isolated as nonadherent cells. The nonadherent splenic dendritic cells were resuspended in RPMI at $3 \times 10^5$ cells/ml.

JAWS II and splenic dendritic stimulator cells were irradiated for 40 minutes in a $^{137}$Cs irradiator (Gammacell 40, Nordion International Inc., Kanata, Ontario, Canada) at 550 rads/min before use in the MLR.

ii. Preparation of responder cells (T cells)

Spleens and lymph nodes were removed from C57Bl/6 or BALB/c mice (Jackson Labs, Bar Harbor, Me.). Spleen cell suspensions in BSS-BSA buffer were made by mechanical disruption of the spleen between glass slides. Red blood cells were lysed by resuspending the spleen cell pellet in 0.9 ml dH$_2$O followed quickly by addition of 0.1 ml 10× HBSS. Lymph node cell suspensions in BSS were made by teasing the nodes with sterile forceps and were pooled with the autologous spleen cell suspension and filtered through nylon cloth filters to remove debris.

The single cell suspension of spleen and lymph node cells was loaded onto a nylon wool column pre-equilibrated at 37° C. with BSS+5% FBS. After incubation at 37° C. for 45 minutes, the T cells were eluted with 37° C. BSS+5% FBS (12 ml per 1.5 g nylon wool column loaded with approximately $1.5 \times 10^8$ total spleen+lymph node cells). The T cells (usually 80–90% pure) were resuspended in RPMI at $3 \times 10^6$ cells/ml.

iii. Incubation conditions for MLR $3 \times 10^5$ responder cells per well (96-well plate) were mixed in duplicate with increasing numbers of irradiated stimulator cells (usually $3 \times 10^3$, $1 \times 10^4$, $3 \times 10^4$ cells) in a final volume of 200 µl. Controls included responder cells alone and stimulator cells alone. A syngeneic MLR includes responder and stimulator cells from the same mouse strain (e.g., C57Bl/6 or BALB/c), whereas an allogeneic MLR has stimulator cells incubated with responder cells from a different strain (e.g., C57Bl/6 or JAWS II stimulator cells with BALB/c responder cells). The MLR cultures were incubated at 37° C. for approximately 72–76 hours before addition of 1 µCi/well $^3$H-thymidine to assay proliferation of responder cells. Cultures were harvested 16–20 hours later with a Skatron cell harvester (Skatron, Sterling, Va.), and the incorporated $^3$H-thymidine was determined with a Wallac Betaplate liquid scintillation counter (Pharmacia).

Figure 1:
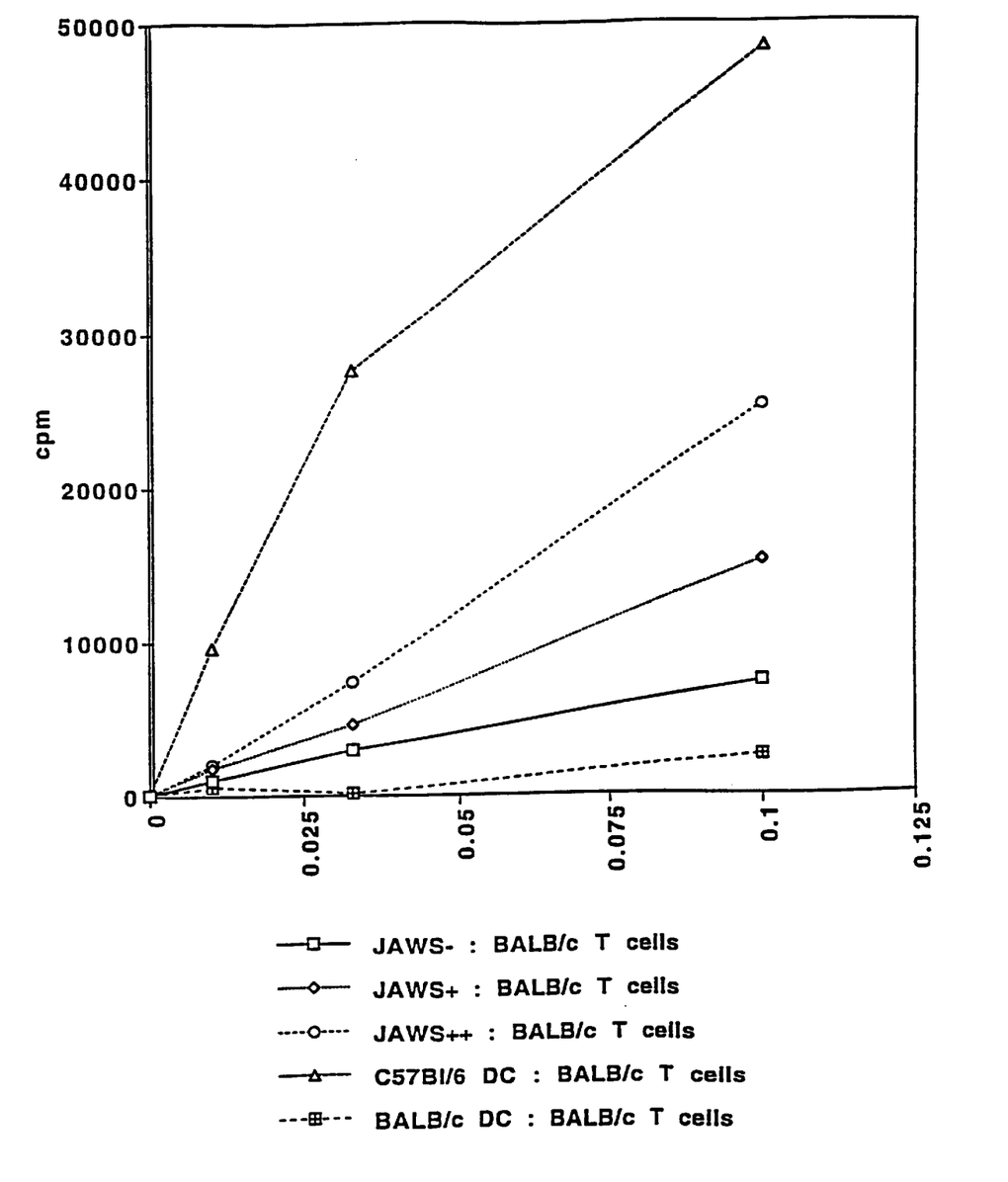
The FIGURE illustrates that allogeneic T cells are stimulated to proliferate when exposed to activated JAWS II cells. The stimulation of the allogeneic T cells is highest when JAWS II is induced with TNF-α, IFN-γ, and IL-4 (JAWS++), but still was present in JAWS II cells induced with TNF-α and IFN-γ (JAWS+) and JAWS II induced with TNF-α alone (JAWS-). Syngeneic BALB/c dendritic cells, used as a negative control, did not stimulate proliferation of the BALB/c T cells.

The results, illustrated in the FIGURE, demonstrate that when JAWS II cells are induced with a combination of factors they will stimulate allogeneic T cells to proliferate. The degree of stimulation is dependent upon the factors used to induce activation of the cell line. The FIGURE shows that stimulation of allogeneic T cells is highest when JAWS II is induced with TNF-α, IFN-γ, GM-CSF and IL-4. In addition, the JAWS II cell line did not stimulate proliferation in syngeneic cells.

EXAMPLE V

Isolation of Immortalized Prostatic Epithelial and Stromal Lineage Cell Lines

Prostate tissue contains epithelial and stromal cells. There are three subtypes of epithelial cells: (1) secretory luminal cells, which line the prostate ducts, express cytokeratins 8 and 18, and in humans, produce PSA and other prostatic products; (2) basal cells, which rest on the basement membrane, express cytokeratins 5 and 14, (and are considered by some to be the "stem" cells) (Peehl et al., *Cell Tissue Res.* 277, 11–18 (1994); and (3) endocrine/paracrine cells, which reside among the secretory cells in all parts of the prostate. The origin and function of these cells are currently unknown. They can be identified by the expression of chromogranin A (Bonkhoff & Remberger, *The Prostate* 28, 98–106 (1996)). Stromal cells are subdivided into fibroblasts (detected by prolyl 4-hydroxylase) and smooth muscle cells (detected by smooth-muscle actin) (Kassen et al., *The Prostate* 28, 89–97 (1996).

Prostatic epithelial and stromal cells can be obtained from mammals such as P53-deficient mice by established procedures. See Orlowski et al., *J. Androl.* 3:232–240; Montpetit, *Prostate* 15, 315–325; Turner, *In Vitro Cell Dev. Biol.* 26, 722–730; Kassen, *Prostate* 28, 89–97. Prostatic tissue is minced into small fragments, and the fragments digested with 1% collagenase, 1% trypsin and 0.1% hyaluronidase at 37° C. for 3–4 hr. The cells are collected by centrifugation and added to the top of a preformed Percoll density step gradient. Cells from different fractions of the gradient are plated on fibronectin-coated plates in RPMI 1640 medium containing 10% fetal calf serum and characterized by their morphology. Cells with an epithelial morphology are grown in DMEM/F12 medium containing 10 ng/ml cholera toxin, 10 ng/ml epidermal growth factor, 4 µg/ml insulin, 10 µg/ml transferrin, 1 µg/ml hydrocortisone, 1 µg/ml dihydrotestosterone, 100 µg/ml bovine pituitary extract, 100 µM phosphoethanolamine, 30 nM selenous acid, and 2.3 µM α-tocopherol. Turner et al., supra; Peehl et al., In Vitro *Cell Dev. Biol.* 24, 530–536.) Cells without an epithelial morphology (stromal cells) are grown in RPMI 1640 medium supplemented with 10% fetal bovine serum (Kassen, supra). Cells surviving about 80 passages are immortalized. Cells can be verified for retention of differentiation markers at intervals through the passaging. Immortalized cell lines can be promulgated from isolates of the surviving cells. The identity of the cell types isolated is verified by immunostaining with antibodies to cytokeratins (epithelial cells), smooth-muscle actin (smooth muscle cells), and prolyl-4-hydroxylase (fibroblasts). The three types of epithelial cells can be distinguished by the differentiation markers noted above. Peehl et al., supra; Bonkhoff & Remberger, supra; Kassen et al., supra.

In addition to the general uses of immortalized cell lines discussed elsewhere in the application, the above cell lines are useful for screening compounds for activity in either inducing or inhibiting prostatic cancer. The compound under activity is incubated with the cell line, optionally, in the presence of a known carcinogen, and the resulting cells are tested for acquisition of a neoplastic phenotype. This phenotype can be recognized from the capacity of neoplastic cells to confer tumors when injected into experimental animals. Compounds that inhibit formation of neoplastic cells are candidates for treating prostatic cancer. Compounds that promote formation of neoplastic cells should be avoid as components of food and drugs.

EXAMPLE VI

Isolation of Immortalized Cardiac Mtocyte Lineage Cell Lines

Cardiocytes can be prepared from mammals, such as p53-deficient mice, according to standard procedures, e.g., Marino et al., *Am. J. Anat.* 186, 127–132 (1989); In Vitro *Cell Dev. Biol.* 26, 229–236 (1990). Cardiocytes can be cultured in M-199 medium (Gibco) with 10% fetal bovine serum, 0.01 μM insulin, and antibiotics (e.g., 250 mM streptomycin or penicillin). Clonal cells are isolated from primary cultures and tested for differentiation markers characteristic of cardiac myocyte lineage cells. Cells are then tested for immortality by their capacity to survive a large number (e.g., about 80) passages, and retain differentiation markers.

Immature cardiac myocyte lineage cell lines can be selected by detection of a set of differentiation markers including skeletal muscle α-actin mRNA (Bishopric et al., *J. Clin. Invest.* 80, 1194–1199 (1987)), nuclear proliferating cell nuclear antigen (PCNA) and smooth muscle cell actin (Ruzika et al., *J. Cell. Biol.* 107, 2575–2586 (1988)). PCNA levels decline after birth in the cytoplasm and are absent from the nucleus of adult cells. Marino et al., *Anatomical Record* 245, 677–684 (1996). The presence of PCNA in the nucleus is therefore a marker of immature myocytes.

Immature cell lines can be induced to differentiate by treatment with thyroid hormone (Klein et al., *J. Clin. Invest.* 77, 1694–1698 (1986), aFGF, bFGF, PDGF, TNFα, GFβ1 or fibroblast conditioned medium and combinations thereof (Hong et al., *Cell Regulation* 2, 1081–1095 (1991)). Differentiated cells express a set of differentiation markers including cardiac α-actin mRNA which predominates over the skeletal muscle α-actin mRNA present in immature cells (Bishopric et al., supra) myosin light chain and atrial natriuretic factor (Miller-Hance et al., *J. Biol. Chem.* 268, 25244–25252 (1993)), type B natriuretic factor (Boer, *Biochem. Biophys. Res. Commun.* 199, 954–961 (1994)), α-cardiac myosin heavy chain (Sanchez et al., *J. Biol. Chem.* 266, 22419–22426 (1991)), phopholamban, (Ganim et al., *Circ. Res.* 71, 1021–1030 (1992)) and spontaneous contractility (Metzger et al., *J. Cell Biol.* 126, 701–711 (1994)).

In addition to the general uses of immortalized cell lines discussed above, cardiac myocyte lineage cell lines and cardiac cells produced by inducing such cell lines to differentiate are useful for screening compounds for potential activity in promoting or inhibiting cardiac damage. The compound being tested is incubated with the cell line or cells produced from it, optionally in combination with an agent known to promote cardiac damage. Damage or protective activity can be monitored from proliferation capacity of the myocytes. Proliferation can be determined by chemosensitivity to neutral red dye (Cavanaugh et al., *Investigational New Drugs* 8, 347–354 (1990); incorporation of radiolabelled nucleotides (Cook et al., *Analytical Biochem.* 179, 1–7 (1989), incorporation of 5-bromo-2'-deoxyuridine in the DNA of proliferating cells (Porstmann et al., *J. Immunol. Methods* 65, 55–63 (1983); Alley et al., *Cancer Res.* 48, 589–601 (1988); Marshall et al., *Growth Reg.* 5, 69–84 (1995); Scudiero et al., *Cancer Res.* 48, 4827–4833 (1988). Damage can also be assayed by monitored cellular hypertrophy.

Although the foregoing invention has been described in some detail by way of illustration and example for purposes of clarity and understanding, it will be obvious that certain changes and modifications may be practiced within the scope of the appended claims. All references and patent filings cited above are incorporated by reference in their entirety for all purposes to the same extent as if each individual reference or patent filing were so individually denoted.

What is claimed is:

1. A cell line of immortalized growth suppressor gene-deficient mammalian osteoblast lineage cells characterized by a set of differentiation markers including parathyroid hormone-induced cAMP expression, osteocalcin expression, alkaline phosphatase expression and bone mineralization activity, wherein on induction with an agent selected from the group consisting of indomethacin, dexamethasone, ascorbic acid and combinations thereof, the osteoblast lineage cells convert to adipocytes characterized by oil red 0 staining.

2. The cell line of claim 1, wherein the cells are rodent cells.

3. The cell line of claim 2, wherein the cells are mouse cells.

4. The cell line of claim 2, wherein the cells are p53-deficient rodent cells.

5. The cell line of claim 4, wherein the agent is indomethacin.

6. The cell line of claim 1, designated 7F2.

7. Adipocytes characterized by oil red 0 staining produced by treating the 7F2 cell line with an agent selected from the group consisting of indomethacin, dexamethasone, ascorbic acid and combinations thereof.

8. A method of screening a compound for efficacy in treating osteoporosis, the method comprising incubating the compound with the cell line of claim 1 and the inducing agent and monitoring conversion of the cell line to adipocytes, the rate or extent of conversion being inversely related to efficacy of the compound.

9. The method of claim 8, further comprising mixing the compound with a carrier to form a pharmaceutical composition.

10. A method of screening a compound for activity in promoting osteoporosis, the method comprising incubating the compound with the cell line of claim 1 and monitoring conversion of the cell line to adipocytes, the rate or extent of conversion being related to activity in promoting osteoporosis.

11. The method of claim 10, wherein the compound is contained in a food or drug.

12. The method of claim 8, wherein the cell line is designated 7F2.

13. The method of claim 10, wherein the cell line is designated 7F2.

* * * * *